tus, a fact that the conversion ratio of carbon dioxide to urea decreases beyond 200° C., etc.

As a pressure in the urea synthesis zone, there is employed a pressure higher than a urea synthesis equilibrium pressure which is determined from such an $NH_3/CO_2$ molar ratio and reaction temperature. In the process of this invention, a pressure in the range of from 150 to 250 Kg/cm$^2$G is employed.

Under the urea synthesis pressure as described above, it is necessary to use a temperature of from 195° to 210° C. to obtain in a stripping step a urea solution containing 10–15% by weight of unreacted ammonia.

As there are such close relationship as described above among $NH_3/CO_2$ molar ratio, reaction temperature, reaction pressure (in other words, the pressure in the stripping step) and stripping temperature, none of the above process conditions shall exceed their respective ranges.

In this invention, it may be possible to reduce in quantity carbon dioxide and water contained in a gaseous mixture of ammonia and carbon dioxide to be separated in the second separation zone for unreacted materials, by first adjusting the temperature of a urea solution resulting from the stripping step using carbon dioxide and containing 10–15% by weight of unreacted ammonia to 180°–195° C. and then supplying the thus temperature-adjusted urea solution to the second separation zone. This brings about preferable results, which will be described hereinbelow.

Namely, the separation of ammonia takes place with priority in the second separation zone for unreacted materials and, as a result the separation of carbon dioxide and water is reduced there. This, in turn, leads to the following two favorable results.

Firstly, in the second separation zone for unreacted materials, ammonia which requires a small heat quantity for the separation is preferentially separated at a relatively high pressure of 10–30 Kg/cm$^2$G. Carbon dioxide which requires a large heat quantity for the sepration principally remains in the solution in the second separation zone but is separated in a subsequent low pressure separation zone for unreacted materials. Thus, a preferred result has been brought about that, to obtain a urea solution containing the same quantity of remaining unreacted ammonia, the heat quantity required in the second separation zone, which requires steam of a high pressure of 10 Kg/cm$^2$G or higher can be decreased although the heat quantity required in a low pressure separation zone, which can be operated by steam of a low pressure of 5 Kg/cm$^2$G or lower have to be increased instead. Since this low pressure steam of 5 Kg/cm$^2$G or less can be obtained when recovering heat given off upon condensing or absorbing ammonia and carbon dioxide gases which have been separated in the stripping step using carbon dioxide, both high pressure steam introduced into and low pressure steam discharged for the overall urea synthesis system will be reduced.

Secondly, by reducing the water content in the gaseous mixture separated from the second separation zone for unreacted materials, it is possible to reduce the quantity of water to be recycled to the urea synthesis zone. Thus, water which acts adversely on the conversion ratio of carbon dioxide to urea in a urea synthesis reaction is reduced in quantity, thereby achieving a high conversion ratio of carbon dioxide to urea.

As a method for adjusting the temperature of a urea solution supplied from the stripping step using carbon dioxide and containing 10–15% by weight of remaining unreacted ammonia, it is preferable, prior to supplying the urea solution to the second separation zone for unreacted materials, to cause the urea solution to contact with carbon dioxide gas as a stripping agent under adiabatic conditions or to subject the urea solution to a heat exchange with a urea solution of 150°–170° C. drawn out of the second separation zone for unreacted materials. It is not necessary to take the heat out of the system when such a method is adopted. Thus, there does not occur heat loss in the overall urea synthesis process, and, consequently, the economical advantage of the process is not sacrificed.

The effect of the above-described temperature adjustment can be observed when adjusted to a temperature below the stripping temperature of 195°–210° C. Thus, it is unnecessary to limit the thus-adjusted temperature within a specific range from its effect. However, taking into consideration that, when envisaging the overall urea synthesis process, the thus-adjusted temperature can be reached without losing heat, the heat load in the second separation zone must not be increased too much and the effect of the temperature adjustment must be clearly observed, it is preferable to adjust the temperature to a range of 175° to 210° C., especially 180°–195° C.

Moreover, the effect of the heat adjustment will be made more distinct where there is used a rectification column as shown in Japanese Patent Publication No. 20380/1965. Namely, by employing a rectification column, a temperature adjustment of a urea solution obtained from a stripping step results in a temperature adjustment of a gaseous mixture separated in the second separation zone for unreacted materials, whereby meeting the above-described objects of this invention.

The present invention brings about various effects, which will be summarized as follows:

(1) Owing to a high conversion ratio of carbon dioxide to urea, it is possible to reduce in quantity high pressure steam of 10 Kg/cm$^2$G or higher to be introduced into the urea synthesis process;

(2) The hydrolysis of urea and formation of biuret are considerably restrained during the stripping step using carbon dioxide; and (3) It is possible to recover steam at a higher pressure in the urea synthesis process.

Now, an embodiment of this invention is described in accordance with the accompanying drawing.

In the drawing, a urea reactor 1 is supplied with ammonia through a line 12, a part of carbon dioxide through lines 14 and 17, and a solution containing recovered unreacted ammonia and unreacted carbon dioxide through an ejector 11. The urea reactor 1 is operated at a temperature of from 185° to 200° C. and a pressure in the range of from 150 to 250 Kg/cm$^2$G, while maintaining the $NH_3/CO_2$ molar ratio within 3 to 5.

A urea synthesis effluent obtained in the urea reactor 1 is supplied to a first separator 2 for the removal of unreacted materials through a line 13 and is brought into a counter-current contact in the form of falling films with carbon dioxide fed as a stripping agent from the bottom of the separator 2 via lines 14 and 20. Here, the first separator 2 is heated to a temperature of from 195° to 210° C. by steam of 20 Kg/cm$^2$G which is charged through a line 32. The steam, which has been used to heat the first separator 2, is discharged through a line 33 in the form of steam condensate. The resulting

PROCESS FOR PRODUCTION OF ACRYLAMIDE

BACKGROUND OF THE INVENTION

1. Field of the Invention

This invention relates to an improvement in a process for producing acrylamide by reacting acrylonitrile with water in the presence of a copper-based catalyst.

2. Description of the Prior Art

Acrylamide has been used in acrylamide polymers which are useful as papermaking chemicals, flocculents, oil recovery additives, soil hardeners, etc., and also has found extensive use as a comonomer for other polymers. Early production of acrylamide for these uses was by the so-called sulfuric acid process. Recently, a catalytic hydration process which comprises reacting acrylonitrile with water in the presence of a copper-based catalyst was developed and has now superseded the sulfuric acid process in industrial production.

Various copper-based catalysts to be described hereinbelow are used in a liquid phase fixed bed or suspended bed in the hydration of acrylonitrile. In either case, however, the catalysts undergo degradation and lose activity with the lapse of time. In an attempt to remedy this defect, there have been proposed many methods which include the pretreatment of the starting acrylonitrile with an acidic aqueous solution or a cation exchange resin (Japanese Laid-Open Patent Publications Nos. 29154/1975 and 108916/1977), the addition of salts such as NaCl to the acrylonitrile hydration system (U.S. Pat. No. 3,869,511), and the regeneration of the degraded catalyst by a reducing treatment (U.S. Pat. No. 3,645,913).

These prior methods are effective, and as required, some of them may be used in combination as a series of improved methods. In order to increase the utility of this new manufacturing process, it has been desired to develop a more effective method for maintaining the activity of copper-based catalysts.

SUMMARY OF THE INVENTION

It is an object of this invention to provide an improved process for producing acrylamide by catalytic hydration of acrylonitrile with water in the presence of a copper-based catalyst.

Another object of this invention is to increase the economic advantage of acrylamide production by this process by maintaining the activity of the copper-based catalyst over a long period of time.

These objects of the invention are achieved, in a process for production of acrylamide by reacting acrylonitrile with water in the presence of a copper-based catalyst, by the presence of 30 to 10,000 ppm, preferably 30 to 4,000 ppm, of acetone of the reaction system.

DETAILED DESCRIPTION OF THE INVENTION

Examples of the copper-based catalyst used in the process of this invention include:

(A) a combination of a copper ion and metallic copper in the form of copper wire or powder, (B) reduced copper obtained by reducing a copper compound with a reducing agent, (C) decomposed copper obtained by decomposing a copper compound by heat, etc. and (D) Raney copper obtained by leaching a Raney alloy of copper with an alkali, etc. Reduced copper is produced, for example, by (1) a method which comprises reducing copper oxide in the gaseous phase with hydrogen, carbon monoxide or ammonia, (2) a method which comprises reducing a salt or hydroxide of copper in aqueous solution with formaldehyde, hydrazine or sodium borohydride, and (3) a method which comprises reducing a salt of hydroxide of copper in aqueous solution with elemental aluminum, zinc or iron. The main catalytic ingredient of the products of these methods is considered to be elemental copper. The decomposed copper is produced, for example, by (1) a method which comprises thermally decomposing in aqueous alkaline solution copper hydride obtained by treating a copper compound with sodium hypophosphite, etc., (2) a method which comprises thermally decomposing copper formate or copper oxalate, (3) a method which comprises thermally decomposing cluster copper, as shown in Japanese Laid-Open Patent Publication No. 108015/1974, and (4) a method which comprises adding copper acetylide or copper nitride directly to the acrylonitrile hydration system. The main catalytic ingredient of the products obtained by these methods, including the method (4), is considered to be elemental copper. Production of Raney copper is by such methods as (1) a method which comprises leaching a copper-aluminum alloy substantially completely with sodium hydroxide, sulfuric acid, organic amines, etc., and (2) a method which comprises partially leaching a copper-aluminum alloy with sodium hydroxide, sulfuric acid, water, organic amines, etc. to leave part of aluminum together with copper. The main catalytic ingredient in these products is considered to be elemental copper. These copper-based catalysts may be supported on usual carriers such as silica, or may contain metals other than copper, for example chromium or molybdenum.

The copper-based catalysts described above are obtained by the respective methods of preparation, and differ from each other in catalytic activity. It has been ascertained however that with regard to their tendency toward interaction with acetone and impurities and other materials present in the reaction mixture, these copper-based catalysts do not differ from each other with the methods of their preparation, for example the methods (A) to (D) described above. Desirably, contact of these copper-based catalysts with oxygen and oxygen-containing gases should be avoided before and during use, because oxygen impairs their catalytic activity and increases by-products such as ethylene cyanohydrin.

Generally, acrylonitrile produced by ammoxidation of propylene is used as the starting acrylonitrile in the hydration reaction of this invention. This acrylonitrile generally contains acetone, acrolein, oxazole, acetonitrile, propionitrile, methacrylonitrile and cis- and trans-crotonitriles as impurities, and hydroquinone monomethyl ether as a stabilizer.

The catalytic hydration reaction in accordance with this invention is carried out in the following manner part of the water and acetone were recovered from the condenser. The recovered acrylonitrile, water and acetone were recycled to the reactor while avoiding their contact with air. In the above process, the ratio of the freshly fed acrylonitrile to the recycled acrylonitrile was about 1:1 at the initial stage. In continuing the above reaction, the same catalyst was additionally fed at suitable times so as to make up for the reduced activity of the catalyst, and the above acrylonitrile ratio was maintained at about 1:1. When the above reaction was continued for 60 days, the concentration of acetone in the reaction solution and the cumulative amount of the catalyst additionally supplied during this time were as shown in Table 1.

TABLE 1

|  | 30 days later | 60 days later |
|---|---|---|
| Concentration of acetone in the reaction solution (ppm) | 6.1 | 6.3 |
| Cumulative amount of the additionally supplied catalyst (parts by weight) | 620 | 1150 |

EXAMPLES 1 TO 3

The same reaction as in Comparative Example 1 was carried out except that the concentration of acetone in the reaction solution was adjusted to 30, 280, and 3,500 ppm, respectively, by adding a small amount of acetone to acrylonitrile. The reaction was continued for 60 hours in each run. The cumulative amounts of the additionally supplied catalyst were as shown in Table 2.

TABLE 2

| Example | Concentration of acetone in the reaction solution (ppm) | Cumulative amount of the additionally supplied catalyst (parts by weight) | |
|---|---|---|---|
| | | 30 days later | 60 days later |
| 1 | 30 | 440 | 840 |
| 2 | 280 | 410 | 780 |
| 3 | 3500 | 450 | 860 |

It is seen from Table 2 that the amounts of the catalysts additionally supplied in these Examples can be decreased from that in Comparative Example 1.

EXAMPLES 4 AND 5 AND COMPARATIVE EXAMPLE 2

One hundred parts by weight of the same catalyst as used in Comparative Example 1 was charged into a 2-liter stainless steel reactor having a stirrer and a catalyst separator built therein. Acrylonitrile and water from which dissolved oxygen had been removed by using nitrogen gas were fed into the reactor at a rate of 400 and 600 g/hr., respectively, and reacted. The acrylonitrile was synthesized by ammoxidation of propylene and contained 0.1 ppm of acetone. Acetone was added to this acrylonitrile in an amount of 0.9, 2.7 and 10% by weight. The reaction solution was stirred together with the catalyst and became a suspension. The suspension was passed through the catalyst separator, and withdrawn from the reaction as a solution substantially free from the catalyst. This reaction was continued for 14 days, and the conversion of acrylonitrile to acrylamide and the concentration of acetone in the reaction solution were measured. The results are shown in Table 3.

TABLE 3

| Example | Amount of acetone added (%) | Concentration of acetone in the reaction solution (ppm) | Conversion (%) | | |
|---|---|---|---|---|---|
| | | | First day | 7 days later | 14 days later |
| 4 | 0.9 | 3,300 | 69 | 53 | 46 |
| 5 | 2.7 | 10,000 | 66 | 51 | 46 |
| Comp. Ex. 2 | 10 | 38,000 | 52 | 38 | 34 |

EXAMPLE 6

Copper oxide in small pellets was packed into a stainless steel reactor, and reduced with a gaseous mixture of hydrogen and nitrogen at about 200° C. to form reduced copper. Using this catalyst, the same catalytic hydration of acrylonitrile as in Example 1 was carried out. The amount of the catalyst initially charged was 250 parts by weight, and the concentration of acetone in the reaction solution was adjusted to 208 ppm.

The cumulative amount of the additionally supplied catalyst in this reaction was 700 parts by weight 30 days later, and 1330 parts by weight 60 days later.

What is claimed is:

1. In a process for producing acrylamide which comprises catalytically hydrating acrylonitrile with water in the presence of a copper-based catalyst, the improvement wherein during the reaction acetone is adjusted to a concentration of 30 to 10,000 ppm in the reaction solution comprising acrylonitrile, water and acrylamide.

2. The process of claim 1 wherein the concentration of acetone present in the reaction solution is 30 to 4,000 ppm.

3. The process of claim 1 wherein the weight ratio of acrylonitrile to water in the reaction solution is from 60:40 to 5:95, and the reaction is carried out at a temperature of 70° to 150° C.

4. The process of claim 1 wherein the weight ratio of acrylonitrile to water in the reaction solution is from 50:50 to 10:90, and the reaction is carried out at a temperature of 90° to 140° C.

5. The process of claim 1 wherein the conversion of acrylonitrile is 30 to 95%, and the unreacted acrylonitrile and water recovered from the reaction solution by distillation are recycled to the reaction system.

6. The process of claim 1 wherein the concentration of acetone in the reaction solution is adjusted to 30 to 10,000 ppm by adding acetone to the starting acrylonitrile and water, to the reaction solution, or to the recovered distillate to be recycled.

7. The process of claim 1 wherein the concentration of acetone in the reaction solution is adjusted to 30 to 10,000 ppm by distilling the starting acrylonitrile or the unreacted acrylonitrile and water recovered by distillation from the reaction solution to decrease the acetone concentration and thereafter using such starting acrylonitrile or such unreacted acrylonitrile and water having a reduced acetone concentration in the hydration.

8. The process of claim 1 wherein the copper-based catalyst is reduced copper obtained by reducing a copper compound with a reducing agent, or Raney copper obtained by developing a Raney alloy.

9. The process of claim 1, 3, 6, 7, or 8 wherein the acrylonitrile is produced by ammoxidation of propylene.

10. The process of claim 1, 3, 6, 7, or 8 wherein the hydration is conducted in an oxygen-free atmosphere.

11. The process of claim 1 wherein the concentration of acetone in the reaction solution is adjusted to 30 to 10,000 ppm by adding acetone to the starting acrylonitrile.

12. The process of claim 1, 2, 3, or 8 wherein the concentration of acetone in the starting acrylonitrile is less than 0.1 ppm and the concentration of acetone in the reaction is adjusted to 30 to 10,000 ppm by adding acetone to said starting acrylonitrile.

* * * * *